US012758729B2

(12) United States Patent
Rose et al.

(10) Patent No.: US 12,758,729 B2
(45) Date of Patent: Oct. 13, 2026

(54) ENDOTRACHEAL TUBE PLACEMENT LOCK SYSTEM

(71) Applicants: Scott Rose, New York, NY (US); Rasa Zarnegar, New York, IN (US)

(72) Inventors: Scott Rose, New York, NY (US); Rasa Zarnegar, New York, IN (US)

(73) Assignees: Cornell University, Ithaca, NY (US); The New York Presbyterian Hospital, New York, NY (US)

( * ) Notice: Subject to any disclaimer, the term of this patent is extended or adjusted under 35 U.S.C. 154(b) by 504 days.

(21) Appl. No.: 18/241,182

(22) Filed: Aug. 31, 2023

(65) Prior Publication Data

US 2024/0075233 A1 Mar. 7, 2024

Related U.S. Application Data

(60) Provisional application No. 63/403,170, filed on Sep. 1, 2022.

(51) Int. Cl.
*A61M 16/04* (2006.01)
*A61M 25/02* (2006.01)

(52) U.S. Cl.
CPC .... *A61M 16/0497* (2013.01); *A61M 16/0493* (2014.02); *A61M 2025/022* (2013.01); *A61M 2025/024* (2013.01)

(58) Field of Classification Search
CPC .......... A61M 16/0497; A61M 16/0493; A61M 2025/022; A61M 2025/024
See application file for complete search history.

(56) References Cited

U.S. PATENT DOCUMENTS

| | | | |
|---|---|---|---|
| 4,774,944 | A | 10/1988 | Mischinski |
| 5,295,480 | A | 3/1994 | Zemo |
| 6,408,850 | B1 | 6/2002 | Sudge |
| 9,308,340 | B2 | 4/2016 | Bond et al. |
| 11,406,780 | B2 | 8/2022 | Landis et al. |
| 2011/0240034 | A1 | 10/2011 | Ciccone |

(Continued)

FOREIGN PATENT DOCUMENTS

| | | |
|---|---|---|
| CN | 208726492 | 4/2019 |
| CN | 216496921 | 5/2022 |

(Continued)

OTHER PUBLICATIONS

Machine translation of KR-20220115286-A. Access from PE2E Search on Mar. 2026. (Year: 2022).*

(Continued)

*Primary Examiner* — Joseph D. Boecker
*Assistant Examiner* — Jaeick Jang
(74) *Attorney, Agent, or Firm* — Barnes & Thornburg

(57) ABSTRACT

An endotracheal tube placement system for securing an endotracheal tube relative to a patient's vocal chords during surgery is disclosed. The system can include a clamp that receives the endotracheal tube and a clamp lock that selectively retains the clamp in a clamped position holding the endotracheal tube in place relative to the clamp. The clamp and clamp lock can be fixed to the mouth area of the patient's face using tape strips. The system may also include positioners sized to be placed between the upper and lower teeth of the patient when the clamp is fixed to a patient's face.

18 Claims, 4 Drawing Sheets

(56) References Cited

U.S. PATENT DOCUMENTS

Figure 1:
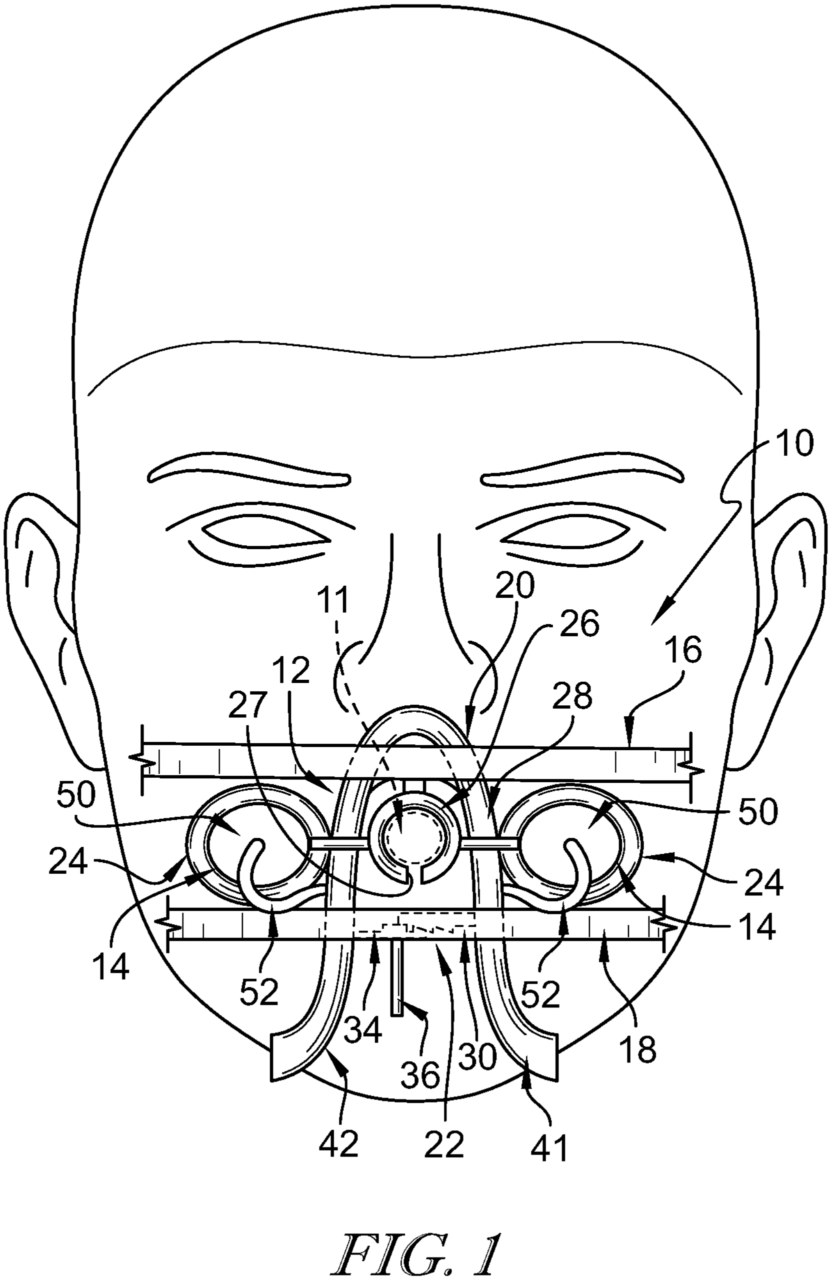

| | | | |
|---|---|---|---|
| 2014/0261463 A1 | 9/2014 | Visconti et al. | |
| 2016/0095995 A1* | 4/2016 | Haider | A61M 16/0493 128/207.14 |
| 2016/0361509 A1 | 12/2016 | Blessing, Jr. et al. | |
| 2020/0222651 A1 | 7/2020 | Jockel et al. | |
| 2021/0008315 A1 | 1/2021 | Drew et al. | |
| 2021/0128860 A1 | 5/2021 | Van Der Vegt et al. | |
| 2021/0275767 A1 | 9/2021 | Ferrandiz Catalan et al. | |
| 2023/0372653 A1* | 11/2023 | Mackinnon, III | A61M 16/0497 |

FOREIGN PATENT DOCUMENTS

| | | | |
|---|---|---|---|
| KR | 101086556 B1 * | 11/2011 | A61M 16/0488 |
| KR | 20220115286 A * | 8/2022 | A61M 16/0488 |
| WO | 2019030368 | 2/2019 | |
| WO | 2022094353 | 5/2022 | |

OTHER PUBLICATIONS

Machine translation of KR-101086556-B1. Accessed from PE2E Search on Feb. 2026. (Year: 2011).*

* cited by examiner

ENDOTRACHEAL TUBE PLACEMENT LOCK SYSTEM

PRIORITY CLAIM

This application claims priority under 35 U.S.C. § 119(e) to U.S. Provisional Application Ser. No. 63/403,170, filed Sep. 1, 2022, which is expressly incorporated by reference herein.

BACKGROUND

About 150,000 thyroid surgeries and 40,000 parathyroid surgeries are performed in the United States per year. There is a lack of devices on the market specifically designed for endotracheal tube stabilization after vocal cord alignment with endotracheal tube surface electrodes.

Precise positioning of endotracheal tube electrodes with the vocal cords is commonly desired in surgeries where the vocal cords are at risk. Vocal chords are innervated by branches of cranial nerve. Neurophysiological techniques sometimes use electromyography (EMG) for monitoring and identification of cranial nerves.

Surgeries that commonly uses this form of interoperative neurological monitoring (IONM) include thyroidectomy, parathyroidectomy, and craniotomy procedures. In the operating room, alignment of endotracheal tube surface electrodes with the vocal cords is often achieved through use of visual observation during intubation.

Some practices and institutions will place rolled up pads in between the teeth on both sides of the ET tube, and then tape down the tube to the face around the upper and lower lip area. Current attempts to maintain ET tube electrode alignment during the course of these operations using such strategies occasionally fails, increasing the likelihood of false positive and false negative EMG feedback.

This can potentially put the patient at risk, which is why the development of a new and improved system is desirable.

SUMMARY

The present disclosure provides for an endotracheal tube placement system. The system can include a clamp, a clamp lock, and at least one optional between-the-teeth positioner. The clamp may be adapted to be coupled to a patient's face via tape or other suitable mechanism. The clamp can be shaped to receive an endotracheal tube in a tube-receiver passageway and can be configured to move from an unclamped position to a clamped position. When the clamp is in the unclamped position, the endotracheal tube is free to slide through the tube-receiver passageway. When the clamp is in the clamped position, the endotracheal tube is engaged by the clamp to resist movement through the tube-receiver passageway. The clamp lock configured to selectively retain the clamp in the clamped position to hold the endotracheal tube in place relative to the clamp.

In illustrative embodiments, the at least one between-the-teeth positioner is sized to be placed between upper and lower teeth of a patient when the clamp is coupled to the patient's face. The at least one between-the-teeth positioner can be coupled to the clamp.

In illustrative embodiments, the at least one between-the-teeth positioner can include left and right positioners movably coupled to the clamp. Each of the at least one between-the-teeth positioner can include a flexible tether coupled to the clamp and a bite member coupled to the flexible tether opposite the clamp. The bite member can be sized to space upper and lower teeth of the patient apart from one another a preselected distance greater than the tube-receiver passageway defined by the clamp.

In illustrative embodiments, the clamp can include a generally U-shape member with two legs (i) that are coupled to one another at a closed end of the clamp and (ii) that are free of one another at a free end of the clamp. The at least one positioner can include left and right positioner holders each coupled to a corresponding left or right leg of the clamp outside the tube-receiver space between the two legs of the clamp. Each of the left and right positioner holders can be shaped to receive a bite member moving therethrough so that each of the left and right bite members can be guided into place between upper and lower teeth of the patient at a location spaced from the endotracheal tube. In some designs, the bite member of each of the at least one between-the-teeth positioner has a generally cylindrical shape and the left and the right positioner holders are each formed to include a round opening sized to correspond to a cross-sectional size of the generally cylindrical shape.

According to another aspect of the present disclosure, an endotracheal tube placement system can include a clamp and a clamp lock. The clamp can be adapted to be mounted relative to a patient's mouth by tape strips or other suitable means. The clamp can have a generally U-shape member with a left leg and a right leg (i) that are coupled to one another at a closed end of the clamp and (ii) that are free of one another at a free end of the clamp. The clamp can be shaped to receive an endotracheal tube in a tube-receiver passageway between the left leg and the right leg. The clamp can further be configured to move elastically from a normally unclamped position in which the endotracheal tube is free to slide through the tube-receiver passageway to a clamped position in which the endotracheal tube is engaged by the clamp to resist movement through the tube-receiver passageway. T clamp lock can be configured to selectively retain the clamp in the clamped position to hold the endotracheal tube in place relative to the clamp and, in turn, the patient's mouth after the tube has been inserted through the clamp and into a patient's throat so as to reduce movement of the endotracheal tube out of a preselected position relative patient biological features.

In illustrative embodiments, the clamp lock is located between the closed end and the free end of the left and the right leg of the clamp and is spaced apart from the free end of the two legs of the clamp. The clamp lock can be provided by a sawtooth fastener having at least one catch tooth coupled to one of the left and the right leg of the clamp and a latch tooth coupled to the other of the left and the right leg of the clamp. The latch tooth can be configured to engage a catch tooth upon movement of the left leg of the clamp toward the right leg of the clamp and thereby hold the clamp in the clamped position.

In illustrative embodiments, the clamp lock can include a release lever that extends from one of the catch teeth or the latch tooth. The release lever can be generally parallel to one of the left leg or the right leg of the clamp. The release lever can be configured to be pressed by a user to disengage the latch tooth from one of a catch tooth freeing the clamp to return to the normally unclamped position from the clamped position. The clamp lock can be located about mid-way between the closed end and the free end of the left and the right leg of the clamp.

In illustrative embodiments, the system can include left and right between-the-teeth positioners. The between-the-teeth positions can be sized to be larger than the endotracheal tube for placement between upper and lower teeth of a patient when the endotracheal tube placement system is arranged over the patient's mouth. The left and right positioners can be movably coupled to the clamp.

In illustrative embodiments, each of the left and the right positioners includes a tether that extends from a corresponding left or right leg of the U-shape member included in the clamp and a bite member coupled to the tether opposite the corresponding left or right leg of the clamp. The bite member can be sized to space upper and lower teeth of the patient apart from one another a preselected distance greater than the size of the tube-receiver passageway.

In illustrative embodiments, the system can include left and right positioner holders coupled to a corresponding left or right leg of the clamp outside the tube-receiver passageway between the two legs of the clamp. Each of the left and right positioner holders can be shaped to receive a bite member moving therethrough so that each of the left and right bite members can be guided into place between upper and lower teeth of the patient at a location spaced from the tube-receiver passageway.

According to another aspect of the present disclosure, an endotracheal tube placement system can include a clamp, a clamp lock, and tape strips. The clamp can be adapted to be mounted relative to a patient's mouth. The clamp can include a endotracheal tube grip that defines a tube-receiver passageway sized to receive an endotracheal tube and a clamp mount that extends upwardly and downwardly from the endotracheal tube grip to provide structure suitable for fixation to a patient above and below the patient's mouth. The clamp can be configured to move elastically from a normally unclamped position in which the endotracheal tube is free to slide through the tube-receiver passageway to a clamped position in which the tube-receiver passageway is sized to engage of the endotracheal tube resisting movement through the tube-receiver passageway. The clamp lock can be configured to retain the clamp in a the clamped position. The tape strips can be adhered to the clamp mount of the clamp at locations spaced above and below the tube-receiver passageway. Tape strips can be adapted to be further adhered to the patient above and below the patient's mouth to fix the clamp to the patient while remaining spaced apart from an endotracheal tube that may be arranged in the tube-receiver passageway.

In illustrative embodiments, the clamp mount is provided by an elastic member having left and right legs arranged along left and right sides of the endotracheal tube grip. The clamp lock can be provided by a sawtooth fastener having a series of catch teeth coupled to one of the left and the right leg and a latch tooth coupled to the other of the left and the right leg. In illustrative embodiments, the clamp lock can include a release lever that extends from one of the catch teeth or the latch tooth generally parallel to one of the left leg or the right leg of the clamp.

In illustrative embodiments, the elastic member of the clamp mount has a U-shape with a closed end and a free end. The clamp lock can be located about mid-way between the closed end and the free end.

In illustrative embodiments, the system can include left and right between-the-teeth positioners. The between-the-teeth positioners can be sized to be placed between upper and lower teeth of a patient when the endotracheal tube placement system is arranged over the patient's mouth. Optionally, the left and right between-the-teeth positioners can be movably coupled to the clamp.

In some embodiments, each of the left and the right between-the-teeth positioners includes a tether that extends from the clamp and a bite member coupled to the tether opposite the clamp. The bite member can be sized to space upper and lower teeth of the patient apart from one another a preselected distance.

In illustrative embodiments, the system includes left and right positioner holders coupled to the clamp. Each of the left and right positioner holders can be shaped to receive a bite member moving therethrough so that each of the left and right bite members can be guided into place between upper and lower teeth of the patient at preselected location relative to the tube-receiver passageway.

In illustrative embodiments, the bite member of each of the left and right positions has a generally cylindrical shape. In some such embodiments, the left and the right positioner holders are each formed to include a round opening sized to correspond to a cross-sectional size of the generally cylindrical shape.

BRIEF DESCRIPTIONS OF THE DRAWINGS

Figure 2:
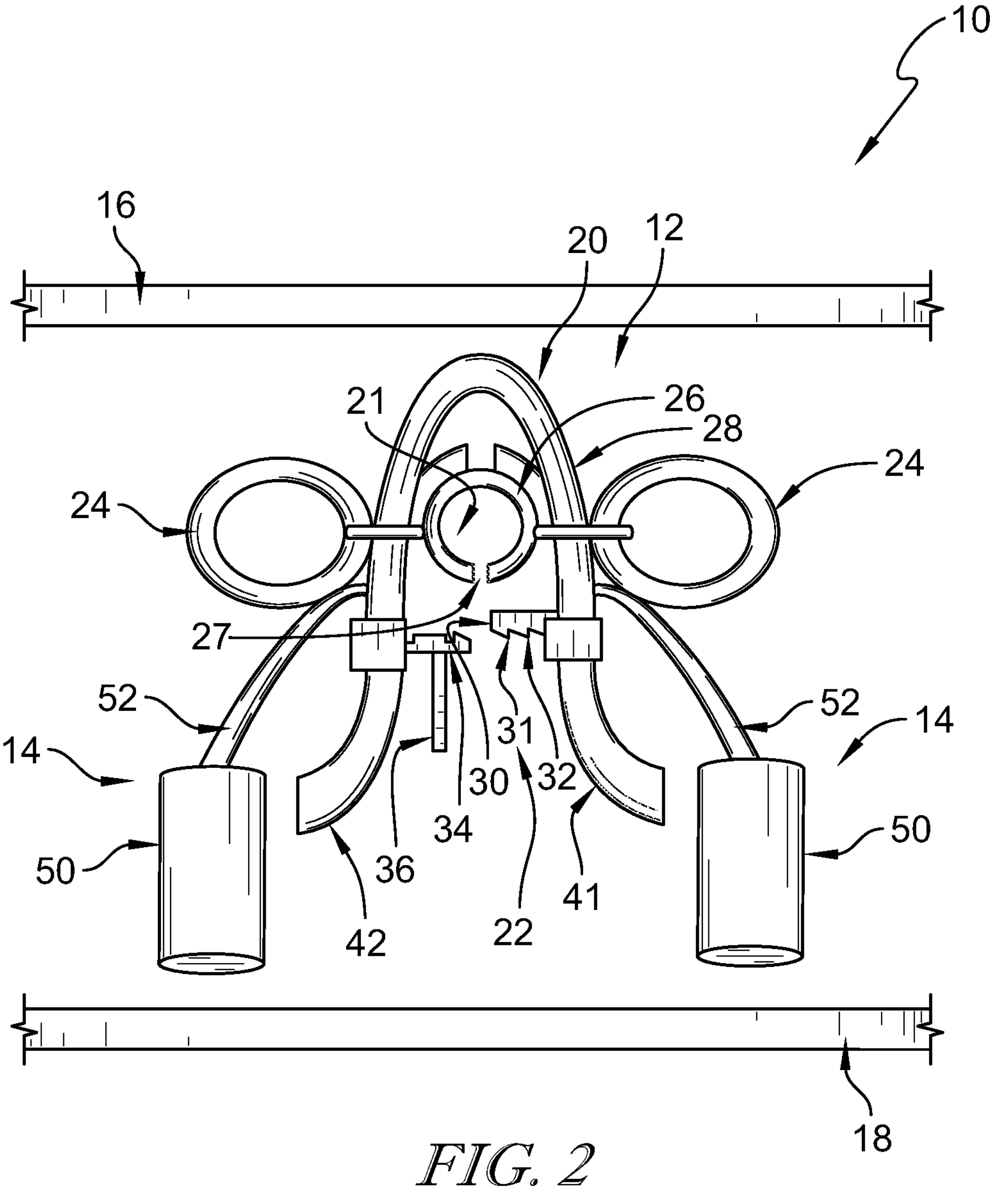
Figure 3:
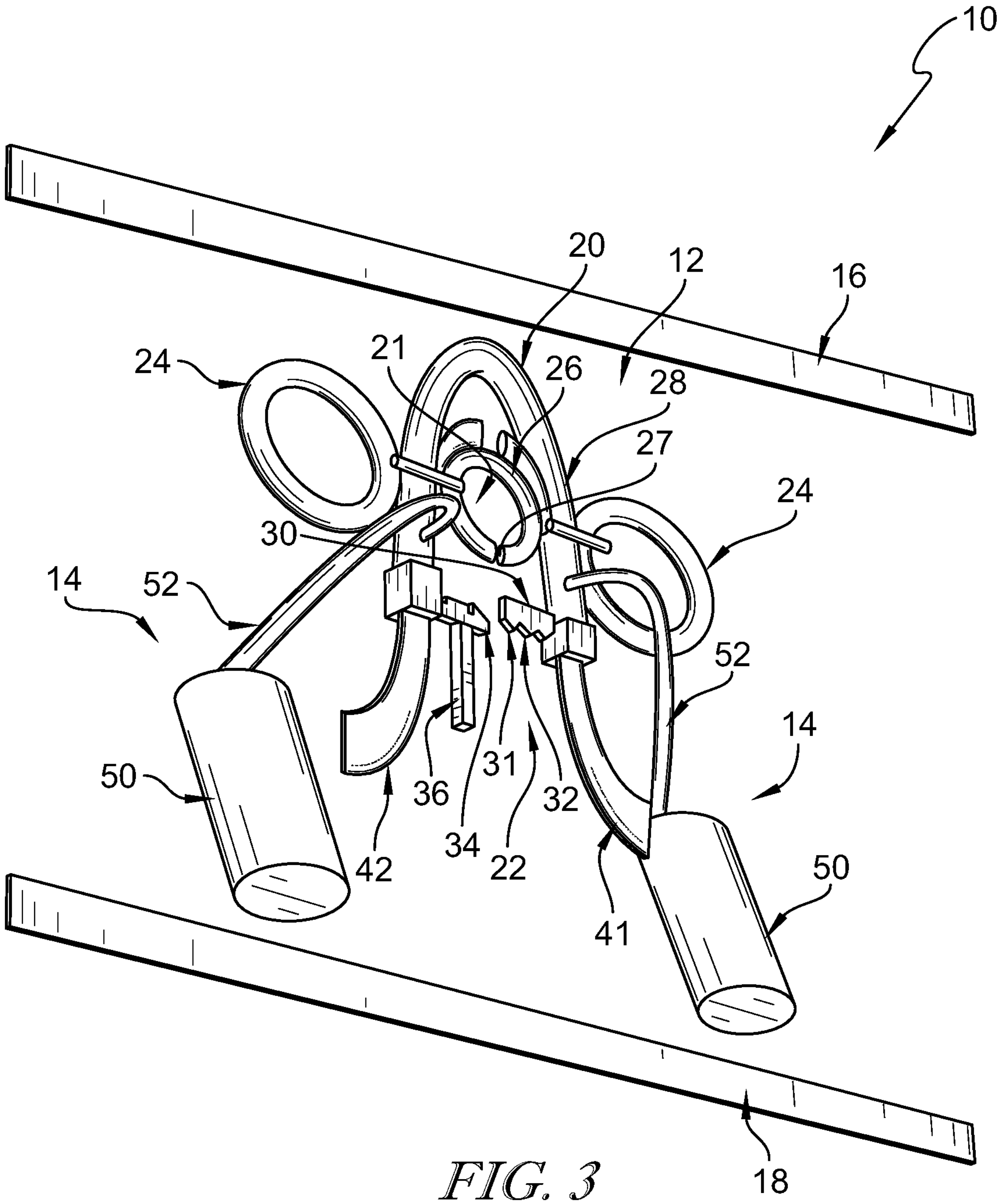
Figure 4:
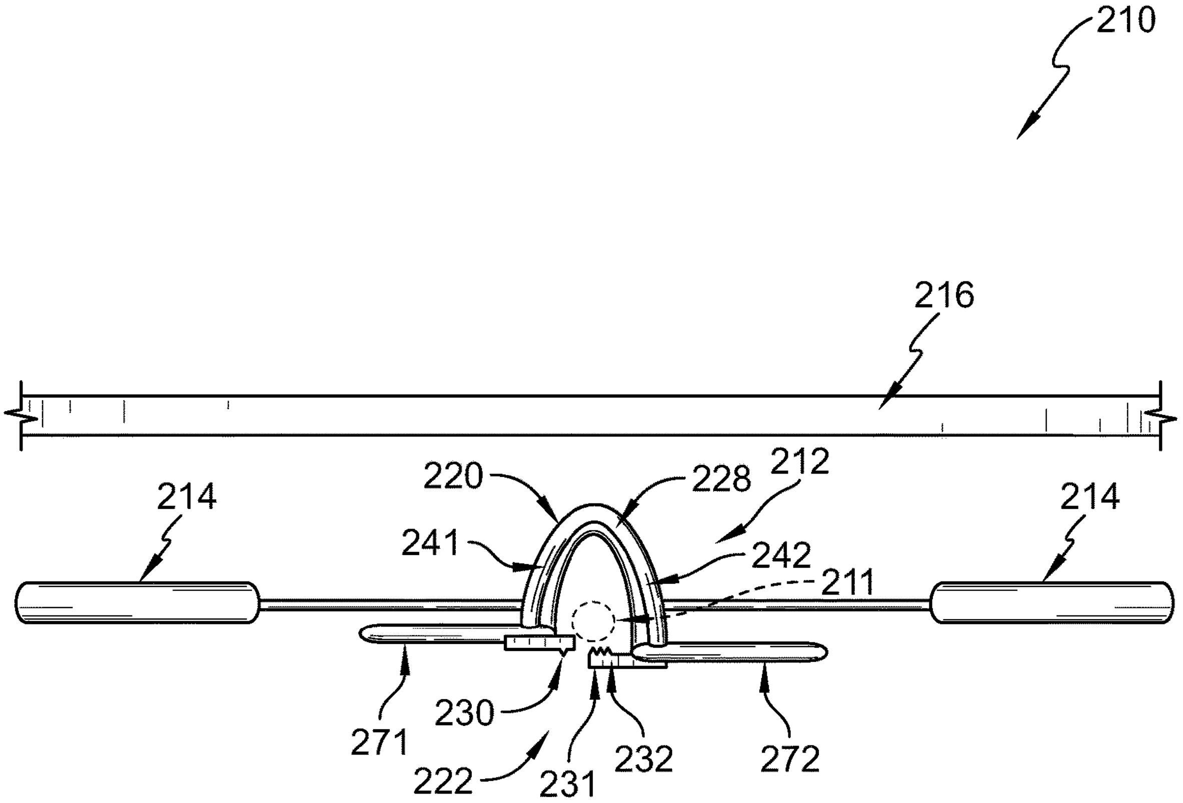

FIG. 1 is a front elevation view of an endotracheal tube placement system shown secured to a patient with a tube locator fixed to the patient via tape strips while clamping an endotracheal tube in a preselected location and holding teeth positioners on both sides of the endotracheal tube to keep the patient's teeth from biting down on the endotracheal tube;

FIG. 2 is a front elevation view of the endotracheal tube placement system of FIG. 1 removed from the patient to show that the tube locator is shaped to include a tube clamp with a tube grip sized to receive the endotracheal tube, a clamp lock for selectively holding the tube clamp in a contracted position engaged with the endotracheal tube, and positioner holders sized to receive between-the-teeth positioners on left and right sides of the tube clamp;

FIG. 3 is a perspective view of the endotracheal tube placement system showing that the tube clamp includes a U-shape member that extends above/below the tube grip to provide locations for the tape strips to fix the tube locator to a patient and showing that the clamp lock extends between free ends of the U-shape member with a number of catch teeth configured to engage a latch tooth having a quick release lever extending therefrom; and FIG. 4 is a front elevation view of another endotracheal tube placement system with a tube locator adapted to be fixed to a patient via a single tape strip while clamping an endotracheal tube in a preselected location and teeth positioners on both sides of the tube locator that are sized to keep the patient's teeth from biting down on the endotracheal tube.

DETAILED DESCRIPTION

An endotracheal tube placement system 10 configured to hold an endotracheal tube 11 in a preselected position relative to a surgical patient is disclosed as suggested in FIG. 1. The system 10 provides means for clamping the endotracheal tube 11 and for taping onto a patient's face at locations spaced apart from the endotracheal tube 11. In addition, the system 10 provides for spacing the patient's teeth so as to avoid biting of the endotracheal tube 11. These and other features are further described within the present application.

In the illustrative embodiment, the system 10 includes a tube locator 12, between-the-teeth positioners 14, and tape strips 16, 18 as shown in FIGS. 1-3. The tube locator 12 engages the endotracheal tube 11 in a releasably clamped fashion. The between-the-teeth positioners 14 are adapted to be placed on left and right sides of the endotracheal tube 11 within a patient's mouth. The tape strips 16, 18 are adhered to the tube locator 12 at locations above and below the endotracheal tube 11 so as to fix the system 10 to a patient's face without directly taping to the endotracheal tube 11.

The tube locator 12 is illustratively made of latex free ABS (Acrylonitrile Butadiene Styrene) plastic. The tube locator 12 is shaped to include a clamp 20, a clamp lock 22, and left/right positioner holders 24 as shown in FIGS. 1-3. The clamp 20 is shaped to define a tube receiver passage 21 sized to be slid down or placed around the endotracheal tube 11 when the clamp 20 is in a normally unclamped position. The clamp 20 is shaped to engage the tube 11 around the tube-receiver passageway 21 when in a clamped position. The clamp lock 22 is configured to selectively retain the clamp 20 in the clamped position. The left and right positioner holders 24 are spaced left and right of the tube-receiver passage 21 and are sized to receive corresponding left/right between-the-teeth positioners 14 as suggested in FIG. 1.

In the illustrative embodiment, the clamp 20 extends upwardly and downwardly from the tube 11 to provide structure over which tape strips 16, 18 can be adhered to the tube locator 12 as shown in FIG. 1. The clamp 20 illustratively includes a tube grip 26 that defines the tube-receiver passageway 21 and a mount member 28 configured to support mounting the clamp 20 to a patient. The tube grip 26 is illustratively provided by a split ring with a gap 27 formed along a bottom side of the ring as shown in FIGS. 2 and 3. The mount member 28 in the exemplary embodiment is a downwardly opening U-shape member forming a channel 29 that receives the tube grip 26.

In other embodiments, the tube grip 26 may be an overlapped ring, a rectangular tube, a triangular tube, or any other suitable shaped grip configured to receive and selectively engage the endotracheal tube 11 around the tube-receiver passageway. Further, the mount member 28 may have other suitable shapes such as an oval or some other closed/open geometry that extends upwardly and downwardly from the tube grip 26 for adhesion to tape strips at locations spaced from the tube 11.

The clamp lock 22 of the illustrative embodiment is configured to selectively retain the clamp 20 in its clamped position as suggested in FIG. 1. The clamp lock 22 includes a sawtooth fastener 30 having a series of catch teeth 31, 32 that engage a corresponding latch tooth 34 when the clamp 20 is in the clamped position. The sawtooth fastener 30 with catch teeth 31, 32 included in the clamp lock 22 are coupled to a right leg 41 of the mount member 28 as shown in FIG. 2. The latch tooth 34 is coupled to a left leg 42 the mount member 28. In the illustrative embodiment, the clamp lock 20 is located about mid-way between a closed end and a free end of the U-shape member that provides the mount member 28.

The clamp lock 22 is further configured to enable release of the clamp 20 from the clamped position to move to its normally unclamped position as suggested in FIG. 2. In the exemplary embodiment, the clamp lock 22 includes a release lever 36 that extends from the sawtooth fastener 30 (or the latch tooth 34) generally parallel to the left leg 42 of the mount member 28. The release lever 36 is configured to be pressed toward the left leg 42 by a user to disengage the latch tooth 34 from the catch teeth 31, 32 freeing the clamp 20 to return to the normally unclamped/released position from the clamped position.

Left and right between-the-teeth positioners 14 are used to space the bottom teeth of a patient from upper teeth so as to avoid biting of the endotracheal tube 11 as suggested in FIG. 1. Each of the positioners 14 includes a bite member 50 and a tether 52. The bite member 50 is illustratively provided by a soft plastic cylinder sized to space upper and lower teeth of the patient apart from one another a preselected distance greater than the tube-receiver passageway 21 defined by the clamp 20. The tether 52, illustratively a flexible cotton string, extends from the bite member 50 to a corresponding one of the right/left legs 41, 42 of the U-shape member that provides the mount member 28. In this way, the positioners 14 are coupled to the tube locator 12. Of course, in other designs, the between-the-teeth positioners 14 can be independent of the tube locator 12 and/or may be provided by other suitable spacers.

In other embodiments, it is contemplated that other between-the-teeth positioners can be incorporated into the system 10. For example, a bite plate, arcuate mouth guard, arcuate teeth trays, and/or other suitable spacers may be used to space upper and lower teeth of the patient apart from one another a preselected distance greater than the tube-receiver passageway 21 defined by the clamp 20.

As noted earlier, the tube locator 12 of the present design includes optional left/right positioner holders 24 provided by rings as shown in FIGS. 1-3. The left/right positioner holders 24 are each coupled to the corresponding left or right leg 41, 42 of the mount member 28 outside a clamp space between the two legs 41, 42. Each of the left and right positioner holders 24 is shaped to receive a bite member 50 moving therethrough so that each of the left and right bite members 50 can be guided into place between upper and lower teeth of the patient at a location spaced from the endotracheal tube 11.

In the illustrative embodiment, an upper tape strip 16 and lower tape strip 18 are used to couple the tube locator 12 to the patient's face as suggested in FIG. 1. The upper tape strip 16 is laid over the mount member 28 at a location spaced above the tube receiving passageway 21. The lower tape strip 18 is laid over the mount member 28 and the clamp lock 22 at a location spaced below the tube receiving passageway 21. In this way, the lower tape strip 18 provides further retention of the clamp 20 in the clamped position.

A second endotracheal tube placement system 210 configured to hold an endotracheal tube 211 in a preselected position relative to a surgical patient is disclosed as suggested in FIG. 4. The system 210 provides means for clamping the endotracheal tube 211 and for taping onto a patient's face at a location spaced apart from the endotracheal tube 211. In addition, the system 210 provides for spacing the patient's teeth so as to avoid biting of the endotracheal tube 211. These and other features are further described within the present application.

In the illustrative embodiment, the system 210 includes a tube locator 212, between-the-teeth positioners 214, and a tape strip 216 as shown in FIG. 4. The tube locator 212 engages the endotracheal tube 211 in a releasably clamped fashion. The between-the-teeth positioners 214 are adapted to be placed on left and right sides of the endotracheal tube 211 within a patient's mouth. The tape strip 216 is adhered to the tube locator 212 at a location above the endotracheal tube 211 so as to fix the system 210 to a patient's face without directly taping to the endotracheal tube 211.

The tube locator 212 is illustratively made of latex free ABS (Acrylonitrile Butadiene Styrene) plastic. The tube locator 212 is shaped to include a clamp 220 and a clamp lock 222 as shown in FIG. 4. The clamp 220 is shaped to define a tube receiver passage 221 sized to be slid down or placed around the endotracheal tube 211 when the clamp 220 is in a normally unclamped position. The clamp 220 is shaped to engage the tube 211 around the tube-receiver passageway 221 when in a clamped position. The clamp lock 222 is configured to selectively retain the clamp 220 in the clamped position.

In the illustrative embodiment, the clamp 220 extends upwardly from the tube 211 to provide structure over which tape strip 216 can be adhered to the tube locator 212. The clamp 20 illustratively includes a U-shape member 228 forming the tube receiver space 221.

The clamp lock 222 of the illustrative embodiment is configured to selectively retain the clamp 220 in its clamped position. The clamp lock 222 includes a sawtooth fastener 230 having a series of catch teeth 231, 232 that engage a corresponding latch tooth 234 when the clamp 220 is in the clamped position. The sawtooth fastener 230 with catch teeth 231, 232 included in the clamp lock 222 are coupled to a right leg 241 of the U-shape member 228. The latch tooth 234 is coupled to a left leg 242 the member 228. In the illustrative embodiment, the clamp lock 220 is located at a free end of the U-shape member 228.

The clamp lock 222 is further configured to enable release of the clamp 220 from the clamped position to move to its normally unclamped position. In the exemplary embodiment, the clamp lock 222 includes quick release pull tabs 271, 272 that extends from the right and left legs 241, 242 of the U-shape member 228. The release pull tabs 271, 272 is configured to be pulled apart by a user to disengage the latch tooth 234 from the catch teeth 231, 232 freeing the clamp 220 to return to the normally unclamped/released position from the clamped position.

Left and right between-the-teeth positioners 214 are used to space the bottom teeth of a patient from upper teeth so as to avoid biting of the endotracheal tube 211 as suggested in FIG. 4. Each of the positioners 214 includes a bite member 250 and a tether 252. The bite member 250 is illustratively provided by a soft plastic cylinder sized to space upper and lower teeth of the patient apart from one another a preselected distance greater than the diameter of the endotracheal tube 211. The tether 252, illustratively a flexible cotton string, extends from the bite member 250 to a corresponding one of the right/left legs 241, 242 of the U-shape member 228. In this way, the positioners 214 are coupled to the tube locator 212. Of course, in other designs, the between-the-teeth positioners can be independent of the tube locator and/or may be provided by other suitable spacers.

In the illustrative embodiment, an upper tape strip 216 is used to couple the tube locator 212 to the patient's face. The upper tape strip 216 is laid over the U-shape member 228 at a location spaced above the endotracheal tube 211.

The endotracheal tube placement systems 10, 210 of the present disclosure are unique in design and offers optimal security after endotracheal tube placement for vocal cord EMG recordings. The system 10 illustratively includes tape strips 16, 18, between teeth positioners 14, a quick release clamp 20 with an attached grip/release strip, and a clip or clamp lock 22.

The quick release clamp grip clip may be made of latex free ABS plastic. The quick release clamp grip clip 20, 220 will grasp the tube endotracheal tube 11, 211 after it is placed, and will be able to click open and click closed The tape strips 16, 18, 216 can be made out of a latex free zinc oxide-based adhesive. The tape strips 16, 18 will lie midline on both the upper and lower lip, and will peel laterally along the face The between teeth positioners 14, 214 may be made out of pliable FDA approved food grade plastic. The between teeth positioners 14, 214 will be placed in the between the teeth in the mouth with one positioner 14, 214 positioned to the left of the tube 11, 211 and the other positioner 14, 214 placed to the right of the tube 11, 211. Cotton string will attach the between teeth positioners 14, 214 to the quick release clamp grip clip. A quick release pull tab will made of latex free ABS plastic will be attached to the quick release clamp grip clip.

According to one method of using the system, before the system is used the endotracheal tube 11, 211 is first placed by the anesthesiologist and the vocal cords are lined up with the placement markers on the tube 11, 211. This tube 11, 211 is held in place by the anesthesiologist while the next steps are executed.

The quick release clamp lever 36 or tabs 271, 272 is pulled open so the endotracheal tube 11, 211 can move past the sawtooth fastener 22, 222 and fit into the tube-receiver space 21, 221. Next, the sawtooth fastener 22, 222 is tightened by pressing the U-shaped member 28, 228 closed until there is a snug and secure fit around the tube 11, 211.

Upon securing the tube 11, 211, the upper tape strip 16, 216 are unrolled and peeled laterally across the face from the upper lip area to the under ear area. Next, in certain embodiments, the lower tape strip 18 is unrolled and peeled laterally across the face from the lower lip area towards the ear lobe The between teeth positioners 14 of certain embodiments are then each passed half way through the between teeth positioner holders 24 on their appropriate side. The between the teeth positioners 14, 214 are then placed between upper and lower teeth of a patient on opposed sides of the tube 11, 211.

The system 10, 210 can be quick release, meaning that if desired the tape can easily be unpeeled and the endotracheal tube 11, 211 can be freed from the tube locator 12, 212 simply by undoing the sawtooth fastener 22, 222. Undoing the sawtooth fastener 22, 222 can be accomplished by pulling on both ends of the pull tabs 271, 272 simultaneously or pressing the sawtooth fastener lever 36. When it's time to extubate or re-adjust the ET tube, the quick release pull tabs 271, 272 are pulled on both ends simultaneously or the sawtooth fastener lever 36 is pressed, and the quick release clamp 20, 220 will open releasing the ET tube.

Two previously used methods to reduce ET tube movement post intubation are through the use of rolled up absorption pads, commonly assembled by the anesthesia team, and tape. Rolled up absorptions pads are aimed at preventing lateral ET tube movement, but tend to become saturated with saliva and unwantingly slip. Tape is attempted to avoid multidimensional ET tube movement, but occasionally have to be unwrapped after placement if the ET tube requires realignment with the vocal cords which is cumbersome.

There are a number of ET tube securing devices produced, although it appears that few, if any, health care systems use these types of devices for vocal cord monitoring. These mechanisms are can include a neck strap, which can cause the tube to shift is the patients body position is manipulated, and/or tape which is not favorable as previously discussed.

In addition to these pitfalls of presently available ET tube securing devises, an additional factor further limiting their usage for vocal cord monitoring is unfavorable cost. Furthermore, none conveniently include positioners to be placed between the teeth which could aid in ET tube stabilization.

Some endotracheal tube holding devices include the Laerdal Thomas ET Tube Holder which uses a neck strap, Dale Medical Products ET Tube Holder Stabilock which uses a neck strap, Hollister Anchorage Oral ET Tube Fastener which uses a neckstrap, Birds and Cronin Endo-MATE ET Holder which uses a neckstrap, B&B Medical Hypoallergenic Tape II ET Holder which uses tape around the tube.

The invention claimed is:

1. An endotracheal tube placement system, the system comprising:

a clamp adapted to be coupled to a patient's face, the clamp shaped to receive an endotracheal tube in a tube-receiver passageway and configured to move from an unclamped position in which the endotracheal tube is free to slide through the tube-receiver passageway to a clamped position in which the endotracheal tube is engaged by the clamp to resist movement through the tube-receiver passageway;

a clamp lock configured to selectively retain the clamp in the clamped position to hold the endotracheal tube in place relative to the clamp; and at least one between-the-teeth positioner sized to be placed between upper and lower teeth of the patient when the clamp is coupled to the patient's face, the at least one between-the-teeth positioner coupled to the clamp, wherein the at least one between-the-teeth positioner includes left and right positioners movably coupled to the clamp, wherein each of the at least one between-the-teeth positioner includes a flexible tether coupled to the clamp and a bite member coupled to the flexible tether opposite the clamp, and wherein the bite member is sized to space upper and lower teeth of the patient apart from one another a preselected distance greater than the tube-receiver passageway defined by the clamp.

2. The system of claim 1, wherein the clamp includes a generally U-shape member with two legs (i) that are coupled to one another at a closed end of the clamp and (ii) that are free of one another at a free end of the clamp, and wherein the at least one positioner includes left and right positioner holders coupled to a corresponding left or right leg of the clamp outside the tube-receiver space between the two legs of the clamp, and wherein each of the left and right positioner holders is shaped to receive a bite member moving therethrough so that each of the left and right bite members can be guided into place between upper and lower teeth of the patient at a location spaced from the endotracheal tube.

3. The system of claim 2, wherein the bite member of each of the at least one between-the-teeth positioner has a generally cylindrical shape and the left and right positioner holders are each formed to include a round opening sized to correspond to a cross-sectional size of the generally cylindrical shape.

4. An endotracheal tube placement system, the system comprising a clamp adapted to be mounted relative to a patient's mouth, the clamp having a generally U-shape member with a left leg and a right leg (i) that are coupled to one another at a closed end of the clamp and (ii) that are free of one another at a free end of the clamp, the clamp shaped to receive an endotracheal tube in a tube-receiver passageway between the left leg and the right leg, and the clamp configured to move elastically from a normally unclamped position in which the endotracheal tube is free to slide through the tube-receiver passageway to a clamped position in which the endotracheal tube is engaged by the clamp to resist movement through the tube-receiver passageway, and a clamp lock configured to selectively retain the clamp in the clamped position to hold the endotracheal tube in place relative to the clamp and, in turn, the patient's mouth after the tube has been inserted through the clamp and into the patient's throat so as to reduce movement of the endotracheal tube out of a preselected position relative to the patient biological features, wherein the clamp lock is located between the closed end and the free end of the left and right legs of the clamp and spaced apart from the free end of the left and right legs of the clamp.

5. The system of claim 4, wherein the clamp lock is provided by a sawtooth fastener having at least one catch tooth coupled to one of the left and right legs of the clamp and a latch tooth coupled to the other of the left and right legs of the clamp, the latch tooth configured to engage a catch tooth upon movement of the left leg of the clamp toward the right leg of the clamp and thereby hold the clamp in the clamped position.

6. The system of claim 5, wherein the clamp lock includes a release lever that extends from one of the at least one catch teeth or the latch tooth generally parallel to one of the left leg or the right leg of the clamp, and wherein the release lever is configured to be pressed by a user to disengage the latch tooth from one of the catch teeth freeing the clamp to return to the normally unclamped position from the clamped position.

7. The system of claim 4, wherein the clamp lock is located about mid-way between the closed end and the free end of the left and right legs of the clamp.

8. The system of claim 4, further comprising left and right between-the-teeth positioners sized to be larger than the endotracheal tube for placement between upper and lower teeth of the patient when the endotracheal tube placement system is arranged over the patient's mouth, the left and right positioners movably coupled to the clamp.

9. The system of claim 8, wherein each of the left and right positioners includes a tether that extends from a corresponding left or right leg of the U-shape member included in the clamp and a bite member coupled to the tether opposite the corresponding left or right leg of the clamp, and wherein the bite member is sized to space upper and lower teeth of the patient apart from one another a preselected distance greater than the size of the tube-receiver passageway.

10. The system of claim 8, further comprising left and right positioner holders coupled to a corresponding left or right leg of the clamp outside the tube-receiver passageway between the two legs of the clamp, wherein each of the left and right positioner holders is shaped to receive a bite member moving therethrough so that each of the left and right bite members can be guided into place between upper and lower teeth of the patient at a location spaced from the tube-receiver passageway.

11. An endotracheal tube placement system, the system comprising a clamp adapted to be mounted relative to a patient's mouth, the clamp including a endotracheal tube grip that defines a tube-receiver passageway sized to receive an endotracheal tube and a clamp mount that extends upwardly and downwardly from the endotracheal tube grip to provide structure suitable for fixation to the patient above and below the patient's mouth, wherein the clamp is configured to move elastically from a normally unclamped position in which the endotracheal tube is free to slide through the tube-receiver passageway to a clamped position in which the tube-receiver passageway is sized to engage of the endotracheal tube resisting movement through the tube-receiver passageway, a clamp lock configured to retain the clamp in the clamped position, and tape strips adhered to the clamp mount of the clamp at locations spaced above and below the tube-receiver passageway, wherein the tape strips are adapted to be further adhered to the patient above and below the patient's mouth to fix the clamp to the patient while remaining spaced apart from the endotracheal tube which has been received in the tube-receiver passageway.

12. The system of claim 11, wherein the clamp mount is provided by an elastic member having left and right legs arranged along left and right sides of the endotracheal tube grip, and wherein the clamp lock is provided by a sawtooth fastener having a series of catch teeth coupled to one of the left and right legs and a latch tooth coupled to the other of the left and right legs.

13. The system of claim 12, wherein the clamp lock includes a release lever that extends from one of the catch teeth or the latch tooth generally parallel to one of the left leg or the right leg of the clamp.

14. The system of claim 12, wherein the elastic member of the clamp mount has a U-shape with a closed end and a free end, and wherein the clamp lock is located about mid-way between the closed end and the free end.

15. The system of claim 11, further comprising left and right between-the-teeth positioners sized to be placed between upper and lower teeth of the patient when the endotracheal tube placement system is arranged over the patient's mouth, the left and right between-the-teeth positioners movably coupled to the clamp.

16. The system of claim 15, wherein each of the left and right between-the-teeth positioners includes a tether that extends from the clamp and a bite member coupled to the tether opposite the clamp, and wherein the bite member is sized to space upper and lower teeth of the patient apart from one another a preselected distance.

17. The system of claim 15, further comprising left and right positioner holders coupled to the clamp, wherein each of the left and right positioner holders is shaped to receive a bite member moving therethrough so that each of the left and right bite members can be guided into place between upper and lower teeth of the patient at preselected location relative to the tube-receiver passageway.

18. The system of claim 17, wherein the bite member of each of the left and right position ers has a generally cylindrical shape and the left and right positioner holders are each formed to include a round opening sized to correspond to a cross-sectional size of the generally cylindrical shape.

* * * * *